US007306915B2

(12) United States Patent
Daito et al.

(10) Patent No.: US 7,306,915 B2
(45) Date of Patent: Dec. 11, 2007

(54) PROBE SET FOR DETECTION OF TARGET SUBSTANCE AND DETECTION METHOD USING THE SAME

(75) Inventors: Motonari Daito, Kobe (JP); Koichi Yamagata, Kobe (JP); Yasuyuki Imura, Kobe (JP)

(73) Assignee: Sysmex Corporation, Hyogo (JP)

( * ) Notice: Subject to any disclaimer, the term of this patent is extended or adjusted under 35 U.S.C. 154(b) by 280 days.

(21) Appl. No.: 11/083,951

(22) Filed: Mar. 21, 2005

(65) Prior Publication Data

US 2005/0208556 A1    Sep. 22, 2005

(30) Foreign Application Priority Data

Mar. 22, 2004  (JP)  ............................ 2004-083732
Mar. 24, 2004  (JP)  ............................ 2004-086958

(51) Int. Cl.
C12Q 1/68      (2006.01)
C07H 21/02     (2006.01)
C07H 21/04     (2006.01)

(52) U.S. Cl. .................. 435/6; 536/23.1; 536/24.3
(58) Field of Classification Search ............... 435/6; 536/23.1, 24.3
See application file for complete search history.

(56) References Cited

U.S. PATENT DOCUMENTS

| 4,882,269 | A | * | 11/1989 | Schneider et al. | ............. 435/6 |
|---|---|---|---|---|---|
| 5,215,899 | A | * | 6/1993 | Dattagupta | ..................... 435/6 |
| 5,437,977 | A | * | 8/1995 | Segev | ............................ 435/6 |
| 5,770,408 | A | | 6/1998 | Sato | |
| 5,854,033 | A | * | 12/1998 | Lizardi | ..................... 435/91.2 |
| 6,261,846 | B1 | | 7/2001 | Usui | |
| 7,169,561 | B2 | * | 1/2007 | Spier | ............................ 435/6 |
| 2003/0175789 | A1 | * | 9/2003 | Weininger et al. | ............. 435/6 |
| 2004/0029142 | A1 | * | 2/2004 | Schon | ........................... 435/6 |
| 2007/0092880 | A1 | * | 4/2007 | Crothers et al. | ............... 435/6 |

OTHER PUBLICATIONS

Baranby, "Genetic Disease Detection and DNA Amplification Using Cloned Thermostable Ligase", Proc. Natl. Acad. Sci. USA, vol. 88, Jan. 1991, pp. 189-193.
Lizardi et al, "Mutation Detection and Single-Molecule Counting Using Isothermal Rolling-Circle Amplification", Nature Genetics, vol. 19, Jul. 1998, pp. 225-232.

* cited by examiner

Primary Examiner—Ethan Whisenant
(74) Attorney, Agent, or Firm—Sughrue Mion, PLLC

(57) ABSTRACT

A probe set is described that includes a first probe having a target-binding substance and a base sequence X1, a second probe having a base sequence X2c and a base sequence X1c hybridizable with the base sequence X1, and a third probe having a base sequence X2 hybridizable with the base sequence X2c. A method for detecting a target substance is also described.

22 Claims, 13 Drawing Sheets

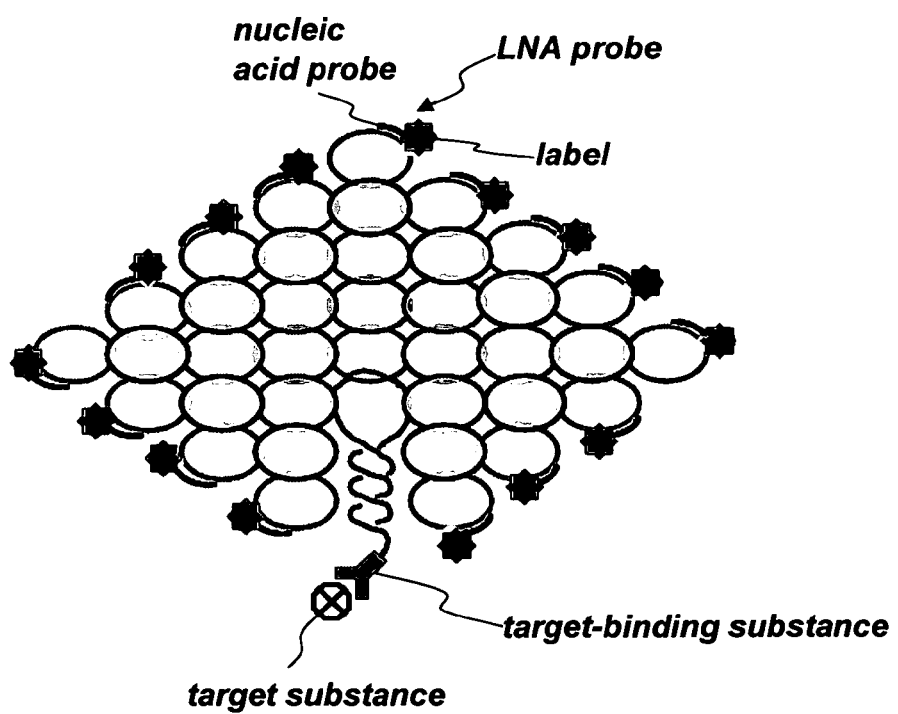

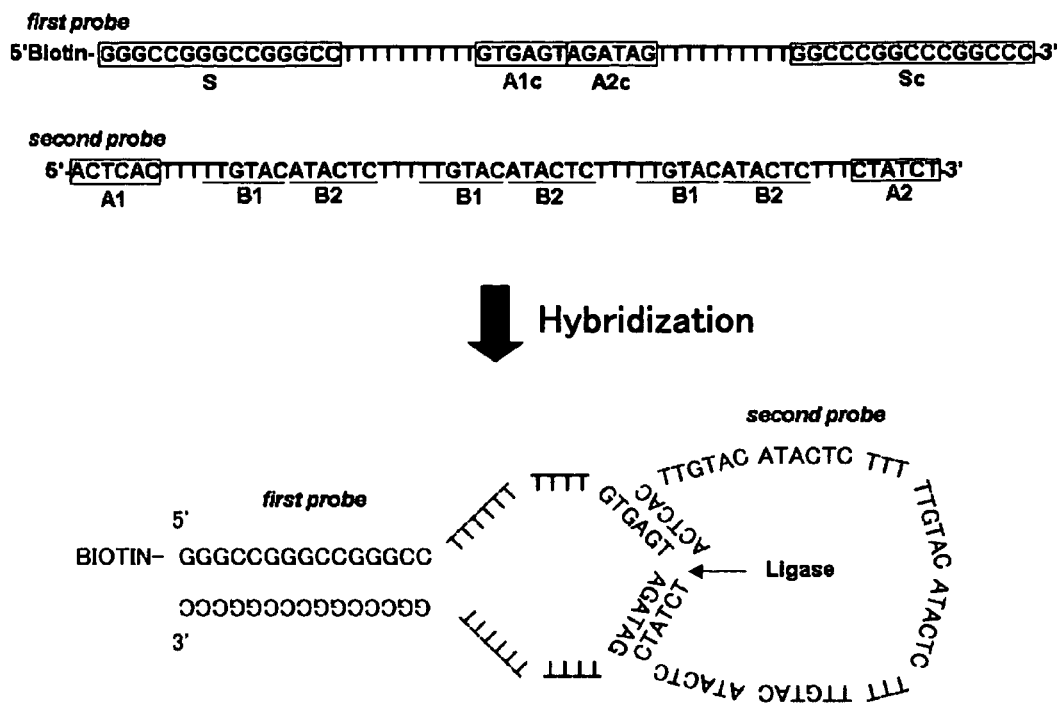

(i) 20bp DNA Ladder (ii) first probe + second probe (iii) first probe

SEQUENCE LISTING

<160> NUMBER OF SEQ ID NOS: 13

<210> SEQ ID NO 1
<211> LENGTH: 20
<212> TYPE: DNA

-continued

```
<213> ORGANISM: Artificial Sequence
<220> FEATURE:
<223> OTHER INFORMATION: chemically synthesized DNA probe for detection

<400> SEQUENCE: 1
gggggaaaaa aaaaaggggg                                                    20

<210> SEQ ID NO 2
<211> LENGTH: 15
<212> TYPE: DNA
<213> ORGANISM: Artificial Sequence
<220> FEATURE:
<223> OTHER INFORMATION: chemically synthesized DNA probe for detection

<400> SEQUENCE: 2 ccccctttttt ttttt                                                        15

<210> SEQ ID NO 3
<211> LENGTH: 15
<212> TYPE: DNA
<213> ORGANISM: Artificial Sequence
<220> FEATURE:
<223> OTHER INFORMATION: chemically synthesized  DNA probe for detection

<400> SEQUENCE: 3
gggggaaaaa aaaaa                                                         15

<210> SEQ ID NO 4
<211> LENGTH: 35
<212> TYPE: DNA
<213> ORGANISM: Artificial Sequence
<220> FEATURE:
<223> OTHER INFORMATION: chemically synthesized  DNA probe for detection
<220> FEATURE:
<221> NAME/KEY: misc_feature
<223> OTHER INFORMATION: biotin molecule between nucleotides 20 and 21

<400> SEQUENCE: 4
gatatggtat aggatatgtt tttcatatcc tatac                                   35

<210> SEQ ID NO 5
<211> LENGTH: 12
<212> TYPE: DNA
<213> ORGANISM: Artificial Sequence
<220> FEATURE:
<223> OTHER INFORMATION: chemically synthesized DNA probe for detection

<400> SEQUENCE: 5
catatcctat ac                                                            12

<210> SEQ ID NO 6
<211> LENGTH: 12
<212> TYPE: DNA
<213> ORGANISM: Artificial Sequence
<220> FEATURE:
<223> OTHER INFORMATION: chemically synthesized DNA probe for detection

<400> SEQUENCE: 6
gatatggtat ag                                                            12

<210> SEQ ID NO 7
<211> LENGTH: 40
<212> TYPE: DNA
<213> ORGANISM: Artificial Sequence
<220> FEATURE:
<223> OTHER INFORMATION: chemically synthesized DNA probe for detection
```

```
<400> SEQUENCE: 7
gatatgagtg actactggtt ggtgtggttg ggtagtcact                              40

<210> SEQ ID NO 8
<211> LENGTH: 12
<212> TYPE: DNA
<213> ORGANISM: Artificial Sequence
<220> FEATURE:
<223> OTHER INFORMATION: chemically synthesized DNA probe for detection

<400> SEQUENCE: 8
catatccatt ag                                                           12

<210> SEQ ID NO 9
<211> LENGTH: 12
<212> TYPE: DNA
<213> ORGANISM: Artificial Sequence
<220> FEATURE:
<223> OTHER INFORMATION: chemically synthesized DNA probe for detection

<400> SEQUENCE: 9
gatatgctaa tg                                                           12

<210> SEQ ID NO 10
<211> LENGTH: 62
<212> TYPE: DNA
<213> ORGANISM: Artificial Sequence
<220> FEATURE:
<223> OTHER INFORMATION: chemically synthesized DNA probe for detection

<400> SEQUENCE: 10
gggccgggcc gggcctttttt tttttgtgag tagatagttt tttttttggc ccggcccggc      60
cc                                                                      62

<210> SEQ ID NO 11
<211> LENGTH: 60
<212> TYPE: DNA
<213> ORGANISM: Artificial Sequence
<220> FEATURE:
<223> OTHER INFORMATION: chemically synthesized DNA probe for detection

<400> SEQUENCE: 11
actcactttt tgtacatact cttttttgtac atactctttt tgtacatact ctttctatct     60

<210> SEQ ID NO 12
<211> LENGTH: 28
<212> TYPE: DNA
<213> ORGANISM: Artificial Sequence
<220> FEATURE:
<223> OTHER INFORMATION: chemically synthesized DNA probe for detection

<400> SEQUENCE: 12
ctatctcact cacaaactat ctactcac                                          28

<210> SEQ ID NO 13
<211> LENGTH: 60
<212> TYPE: DNA
<213> ORGANISM: Artificial Sequence
<220> FEATURE:
<223> OTHER INFORMATION: chemically synthesized DNA probe for detection

<400> SEQUENCE: 13
gtacaatttg tgagtagata gtttgtgagt agatagtttg tgagtagata gtttgagtat      60
```

PROBE SET FOR DETECTION OF TARGET SUBSTANCE AND DETECTION METHOD USING THE SAME

BACKGROUND

1. Field of the Invention

The present invention relates to a probe set for detecting a target substance in a sample and a method of detecting a target substance by using the same.

2. Description of the Related Art

Conventionally, Southern hybridization, Northern hybridization, in situ hybridization, etc. have been well known as a method of detecting a target nucleic acid in a sample. These are methods of detecting the presence and/or position of a target nucleic acid by hybridizing a labeled probe with the target nucleic acid which is blotted in a membrane or is in a fixed cell, and then detecting the signal generating from the labeled probe. These methods do not involve amplification of a target nucleic acid, so that particularly when the amount of the target nucleic acid in a sample is very low, the signal is weak and the detection sensitivity is low.

As one method of detecting a nucleic acid in a sample by amplifying the nucleic acid, a method described in U.S. Pat. No. 5,770,408 can be used. This method involves the following steps. A target nucleic acid-containing sample, probe A, and probe B are mixed to prepare a reaction mixture. Probe B is hybridized cyclicly with the target nucleic acid, and the 5'- and 3'-ends of probe B are ligated by a ligase with each other. The reaction mixture is heated to a high temperature of 90° C. or more to thermally denature the hybridization product of the target nucleic acid and probe B. Upon thermal denaturation, the hybridization product can have a structure wherein the single-stranded target nucleic acid penetrates the cyclic probe B. By decreasing the temperature of the reaction mixture, the probe A is hybridized cyclicly with the cyclic probe B, and the 5'- and 3'-ends of probe A are ligated by a ligase with each other. In this manner, the probes A and B are bound linearly to one molecule of the target nucleic acid. The probes A and B bound to the target nucleic acid are labeled, whereby the nucleic acid contained even in a very small amount in a sample can be detected with a strong signal.

However, the target in the above method is limited to nucleic acid, and other substances such as protein cannot be detected. In addition, the step of thermally denaturing the reaction mixture at a high temperature of 90° C. or more is necessary, thus necessitating an apparatus for keeping the reaction mixture at a high temperature for a predetermined time.

SUMMARY

The present invention provides a probe set capable of detecting, with a strong signal, a target substance such as a nucleic acid, a protein, a hapten or the like in a sample and a method of detecting a target substance, which does not necessitate a step of thermal denaturation.

The scope of the present invention is defined solely by the appended claims, and is not affected to any degree by the statements within this summary.

A first aspect of the present invention relates to a probe set includes:

a first probe having a target-binding substance and a base sequence X1, a second probe having a base sequence X1c and a base sequence X2c, the base sequence X1c hybridizable with the base sequence X1, and a third probe having a base sequence X2 hybridizable with the base sequence X2c.

A second aspect of the present invention relates to a method for detecting a target substance includes:

(a) preparing a first probe having a target-binding substance and a base sequence X1, a second probe having a base sequence X2c and a base sequence X1c hybridizable with the base sequence X1, and a third probe having a base sequence X2 hybridizable with the base sequence X2c;

(b) binding the target-binding substance to a target substance;

(c) hybridizing the second probe with the first probe; and (d) hybridizing the third probe with the second probe.

A third aspect of the present invention relates to a probe set includes:

a first probe having a target-binding substance and a base sequence X12 of base sequences X1 and X2 adjacent to each other, a second probe having at one end a base sequence X1c hybridizable with the base sequence X1, having at the other end a base sequence X2c hybridizable with the base sequence X2, and having in a region not containing the both ends a base sequence Y12c of base sequences Y1c and Y2c adjacent to each other, and a third probe having at one end a base sequence Y1 hybridizable with the base sequence Y1c and at the other end a base sequence Y2 hybridizable with the base sequence Y2c.

BRIEF DESCRIPTION OF THE DRAWINGS

FIG. 2 shows the case where the nucleic acid of each probe is DNA. In FIG. 2(a), the "first probe" is SEQ ID NO: 1, the "second probe" is SEQ ID NO:2, and the "third probe" is SEQ ID NO:3. In FIG. 2(b), the upper strand is two second probes aligned end to end, hybridized to a first probe (lower strand), along with free second probe (left side) and free third probe (right side). FIG. 2(c) shows the further alignment of additional second probes end to end (upper strand), hybridized to the first probe (left side of lower strand) which is further aligned with two third probes (aligned in reverse orientation end to end, right side of lower strand). FIGS. 2(d) and (e) are the same as FIG. 2(c), with each of the probes ligated to form an upper and lower strand.

In FIG. 3. the "first probe" is SEQ ID NO:4. the "second probe" is SEQ ID NO:5. and the "third probe" is SEQ ID NO:6. The lower portion of FIG. 3 shows hybridization and ligation of the first probe with three second probes (aligned end to end on the right side of the upper strand) and three third probes (aligned end to end on the right side of the lower strand).

FIG. 9 shows a schematic illustration of the reaction in Experiment 2-1. In FIG. 9, the "first probe" is SEQ ID NO:10 and the "second probe" is SEQ ID NO:11. The lower portion of FIG. 9 shows the first probe in a stem-loop formation hybridized to the 5' and 3' ends of said second probe.

DESCRIPTION OF THE PREFERRED EMBODIMENTS

Figure 1:
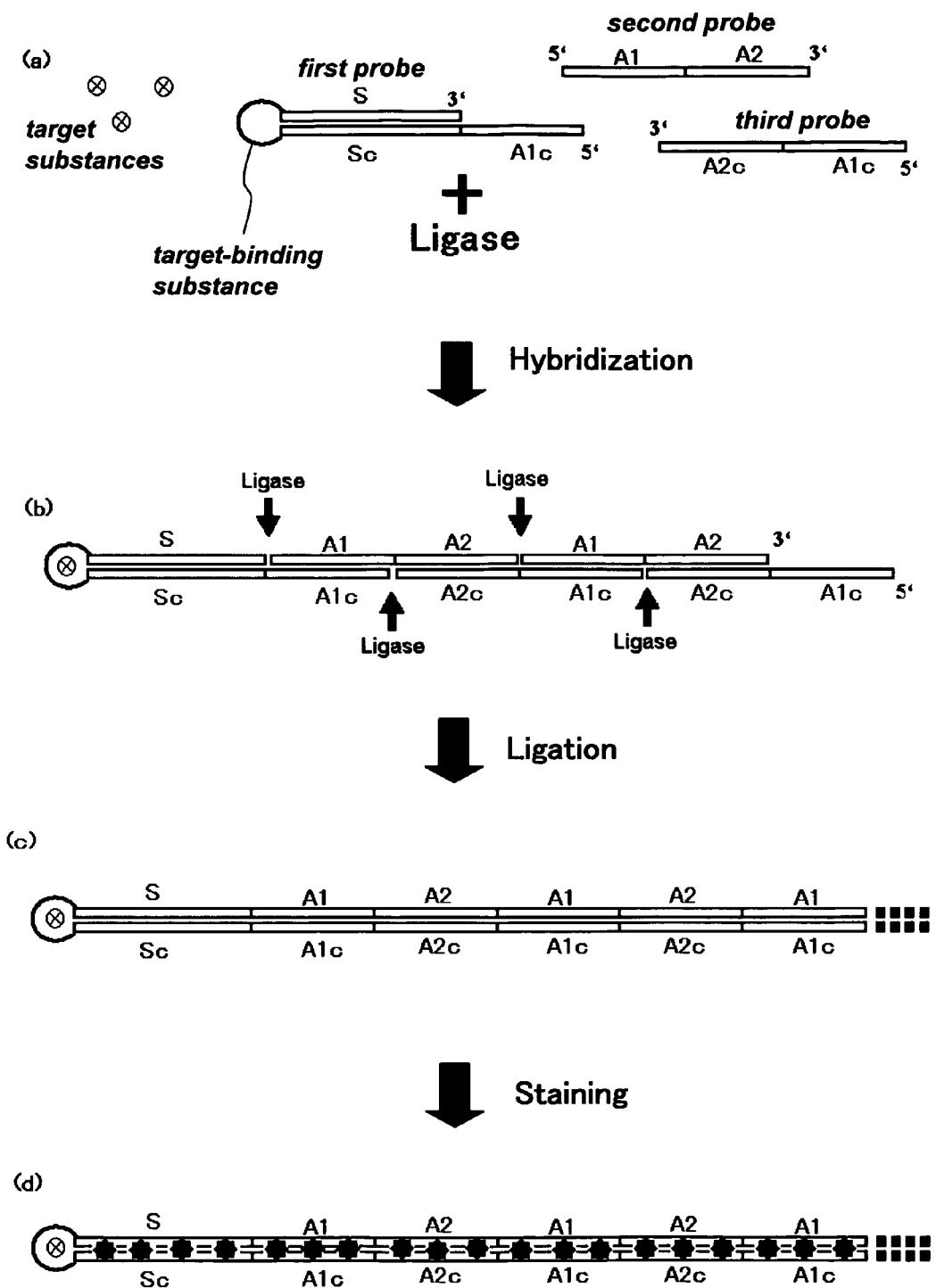
FIG. 1 shows a schematic illustration showing a detection principle in a stage before the respective probes are bound to form a linear complex for detection.

The term "nucleic acid" in the present specification includes not only DNA and RNA but also artificially synthesized nucleic acid (referred to hereinafter as artificial nucleic acid) such as PNA (peptide nucleic acid), BNA (bridged nucleic acid), and analogues thereof The term "base sequence" in the present specification includes not only base sequences of DNA and RNA but also base sequences of artificial nucleic acids such as those of PNA, BNA, and analogues thereof.

<Target Substance>

The target substance detected by the probe set of the present invention is not particularly limited. Examples of the target substance include nucleic acids, proteins, hormones, neurotransmitters, autacoids, haptens, etc. The target substance may be viruses or cells of microorganisms, pollens, etc.

<Probe Set>

The probe set used in this embodiment contains, for example, 3 kinds of probes, that is, first, second and third probes, as shown in FIG. 1(a) or FIG. 8(a). When a target substance is detected, a complex for detection composed of the target substance and these probes bound thereto is formed.

Hereinafter, the respective probes are described in detail.

(1) First Probe

The first probe has a substance capable of binding to a target substance (hereinafter, referred to as "target-binding substance") and a base sequence A1c. The base sequence A1c can hybridize with a base sequence A1 possessed by the second probe described later.

The target-binding substance is not particularly limited insofar as it is a substance capable of binding to the target substance. For example, when the target substance is a nucleic acid, use is made of e.g. a nucleic acid having a base sequence hybridizable with the target substance. When the target substance is a protein, use is made of e.g. an antibody or aptamer specific to the protein. When the target substance is an antibody, an antigen binding specifically to the antibody may be used. When the target substance is a hormone, a neurotransmitter, an autacoid or the like, use is made of e.g. a receptor capable of binding thereto. When the target substance is a hapten, use is made of e.g. an antibody specific to the hapten. When the target substance is a cell, use is made of e.g. an antibody specific to an externally exposed substance of the cell.

The first probe preferably has a base sequence S and a base sequence Sc hybridizing with the base sequence S. In this case, the base sequence S hybridizes with the sequence Sc so that this part of the first probe forms a double strand to form a stem loop structure. By forming the stem loop structure, the first probe can be stabilized. The length of the base sequence S is not particularly limited insofar as the sequence S can hybridize with the base sequence Sc to form the stem loop structure. The thermal melting point (Tm) of the base sequences S and Sc are preferably higher than the reaction temperature in formation of the complex for detection. Specifically, the length of the base sequence S is preferably 7-mer or more.

(2) Second Probe

The second probe has a base sequence A1 hybridizable with the base sequence A1c of the first probe. The second probe also has a base sequence hybridizable with a base sequence possessed by the third probe described later.

Although the second probe may have an intervening part between these base sequences, the second probe preferably does not have the intervening part. A nucleic acid or a polyether alcohol such as hexaethylene glycol may be used as the intervening part.

(3) Third Probe

The third probe has a base sequence hybridizable with the base sequence of the second probe. Further, the third probe preferably has a base sequence A1c. In this case, the third probe is preferably a structure wherein these base sequences are bound directly to each other, but the probe may have an intervening part between the base sequences. A nucleic acid or a polyether alcohol such as hexaethylene glycol may be used as the intervening part.

The length of each of the sequences described above is not particularly limited, but is preferably a length of 4 to 20 bases, more preferably 4 to 10 bases and most preferably 4 to 8 bases.

<Detection of the Target Substance>

The method of detecting the target substance is not particularly limited, and various methods are conceivable.

For example, there is a method using a plate. According to this method, substances contained in a sample are immobilized on a well of a plate, and the probe set is added to and reacted with the substances. When the target substance is contained in the sample, the probe binds to the target substance immobilized on the well, so that even if the reaction solution is removed, the complex for detection is immobilized on the well.

The complex for detection is labeled as shown below, and on the basis of its signal, the target substance can be detected.

The complex for detection is intercalated with an intercalating fluorescent dye matter such as ethidium bromide, Oregon Green or SYBR GREEN, and the fluorescence of this dye can be used as a signal for detecting the target substance.

By previously binding a fluorescent substance such as FITC to at least one of the probes, the fluorescence of the fluorescent substance can be used as the signal. A radioisotope such as $^{125}$I, $^{32}$P or the like can be bound in place of FITC, and its emitted radiation can be used as the signal.

After alkali phosphatase is bound to at least one probe, the luminescence, fluorescence or coloration generated upon reaction of this enzyme with a luminescent/coloring substance such as digoxigenin or acridinium ester, a luminescent substance such as dioxetane, or a fluorescent substance such as 4-methylumbelliferyl phosphate, can be used as the signal.

After avidin or biotin is bound to at least one probe, while biotin or avidin combined with a fluorescent substance, a coloring substance or the like is bound to the target substance, the fluorescence, coloration or the like generated upon reaction of these substances can be used as the signal.

After a donor fluorescent dye and an acceptor fluorescent dye are bound to at least one probe, their emitted fluorescence using fluorescence resonance energy transfer (FRET) can be used as the signal.

EXAMPLE 1

Probe Set Forming a Linear Complex for Detection

Probes having the following features can be used to form a linear complex for detection in order to detect a target substance in a sample.

(1) First Probe

The first probe has a target-binding substance and a base sequence A1c located at the end of the first probe. The first probe may also have a base sequence Sc adjacent to the base sequence A1c, and a base sequence S hybridizable with the base sequence Sc.

(2) Second Probe

The second probe has base sequences A1 and A2. The second probe is a base sequence of the base sequences A1 and A2 bound to each other.

(3) Third Probe

The third probe has base sequences A1c and A2c. The third probe is a base sequence of the base sequences A2c and A1c bound to each other.

Among the base sequences described above, a pair of base sequences A1 and A1c, a pair of base sequences A2 and A2c, and a pair of base sequences S and Sc are designed respectively to be hybridizable with each other. Thus, the second probe hybridizes with the first probe bound to the target substance, and the third probe further hybridizes therewith, to form a complex for detection. The second and third probes hybridize successively with the complex for detection thereby linearly extending the complex for detection. The type of base constituting each base sequence is not particularly limited.

Because the second and third probes have base sequences hybridizable with each other, it is considered that the second and third probes hybridize with each other without binding to the first probe, thus extending a double-stranded chain of only the second and third probes. However, the base sequence Sc adjacent to the base sequence A1c of the first probe forms a double-stranded chain with the base sequence S, so that upon hybridizing the base sequence A1 of the second probe with the base sequence A1c of the first probe, the end of the second probe adjacent to the end of the base sequence S can due to stacking effect be located more stably than usual. This can also apply when the third probe binds to the complex of the first and second probes. That is, the Tm of the complex of the second and third probes is higher than the Tm of each of the probes in a free form. Accordingly, the binding of the second and third probes to each other in a free form can be minimized by establishing a suitable reaction temperature for reaction of the sample with the probe set, thus suppressing the occurrence of unspecific reaction.

The end of each probe constituting the linear complex for detection is preferably ligated with the end of another probe. The linear complex for detection can thereby be further stabilized to increase durability against decomposition and washing. When the base sequence of each probe is a base sequence of DNA or RNA, the end of each probe can be ligated by a ligase to the end of another probe. When the respective probes are ligated by a ligase, the 5'- or 3'-end of each probe should be previously phosphorylated. When the base sequence of each probe is an artificial nucleic acid, the end of each probe can be ligated by photoligation. As the method of ligating artificial nucleic acids by photoligation, a method described in for example U.S. Pat. No. 6,593,088B1 can be used.

Hereinafter, the method of detecting a target substance by using the probe set forming a linear complex for detection is described in detail by reference to FIG. 1.

FIG. 1 is a schematic illustration showing a detection principle. FIG. 1 shows the case where the nucleic acid of each probe is DNA, but the same detection principle applies to the case where each probe is other nucleic acid such as RNA or artificial nucleic acid.

As shown in FIG. 1(a), a sample containing a target substance, the probe set, and a ligase are first mixed. The first probe has the nucleotide sequence A1c located at the region including the 5'-end of the probe, the nucleotide sequence Sc adjacent to the sequence A1c, and the nucleotide sequence S located at region including the 3'-end of the first probe. A target-binding substance is present between the nucleotide sequences S and Sc. The nucleotide sequences S and Sc are complementary to each other and thus hybridize with each other, and the first probe forms a stem loop structure having the nucleotide sequence A1c protruded at the region including the 5'-end of the probe. The second probe is a polynucleotide wherein the nucleotide sequence A1 located at the region including the 5'-end of the probe is adjacent to the nucleotide sequence A2 located at the region including the 3'-end of the probe. The third probe is a polynucleotide wherein the nucleotide sequence A2c located at the region including the 3'-end of the probe is adjacent to the nucleotide sequence A1c located at the region including the 5'-end of the probe.

In FIG. 1(b), the respective probes are bound to form a complex for detection. First, the nucleotide sequence A1 of the second probe hybridizes with the nucleotide sequence A1c of the first probe. Then, the nucleotide sequence A2c of the third probe hybridizes with the nucleotide sequence A2 of the second probe. Further, the free second probe not hybridizing with the first probe hybridizes with the nucleotide sequence A1c of the third probe. Thereafter, the free second or third probe hybridizes successively with the protruded sequence of the complex for detection to extend the complex for detection. By ligation simultaneous with this extension, the adjacent end of each probe is ligated to form the stable complex for detection as shown in FIG. 1(c).

As shown in FIG. 1(d), the complex for detection is intercalated with an intercalating fluorescent dye such as ethidium bromide, Oregon Green or SYBR GREEN. On the basis of the fluorescence of this dye, the target substance in the sample can be detected. The method of detecting the intercalating fluorescent dye has been illustrated, but other known methods of detecting nucleic acid as described above can also be used.

Hereinafter, the method of detecting a target substance by using a first probe having a different structure from that of the above first probe is described in detail by reference to FIG. 2.

Figure 2:
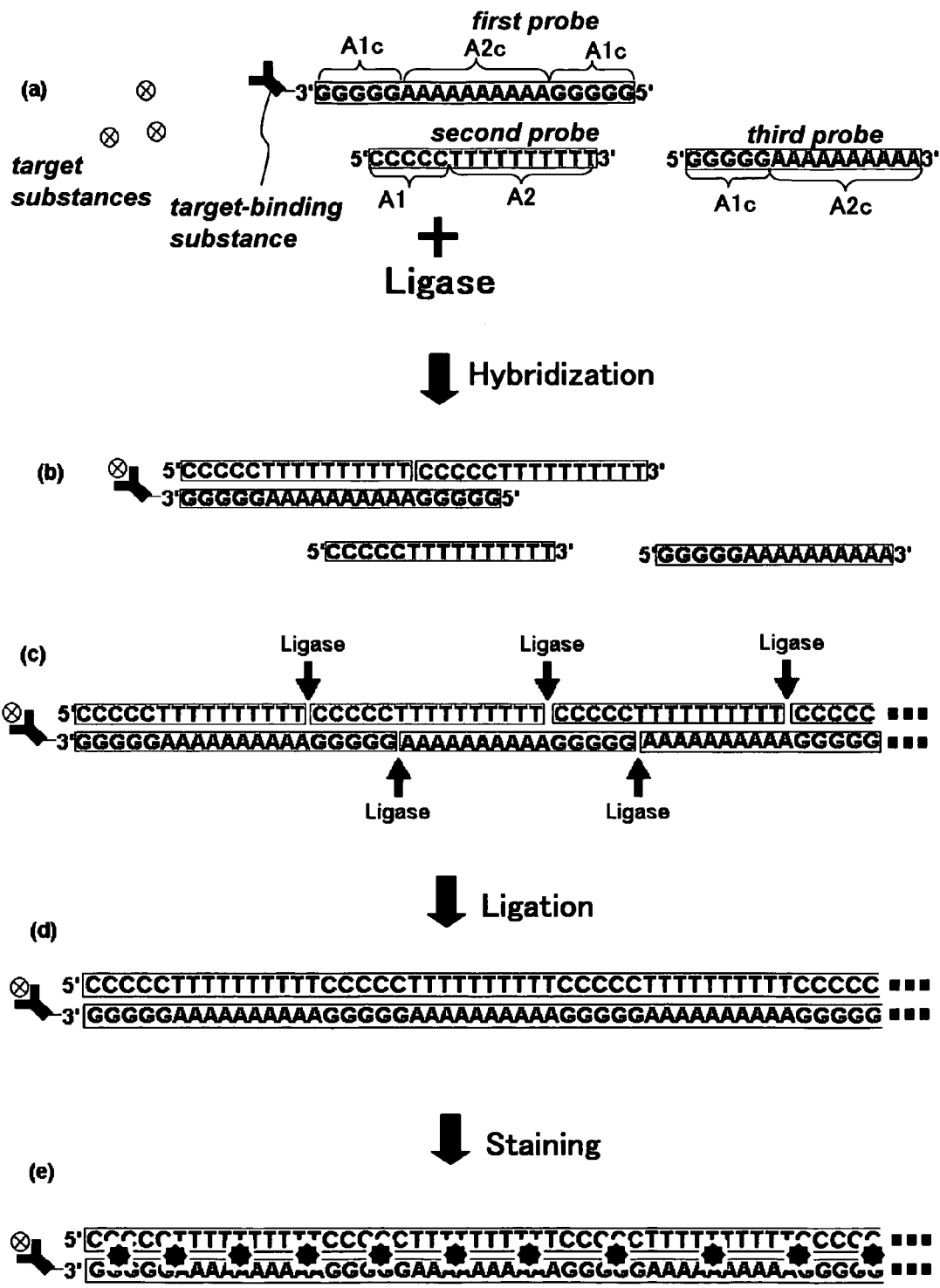
FIG. 2 shows a schematic illustration showing a detection principle in a state before the respective probes are bound to form a linear complex for detection.

FIG. 2 is a schematic illustration showing a detection principle. FIG. 2 shows the case where the nucleic acid of each probe is DNA, but the same detection principle also applies to the case where each probe is other nucleic acid such as RNA or artificial nucleic acid.

As shown in FIG. 2(a), a sample containing a target substance, the probe set, and a ligase are first mixed. The first probe has a nucleotide sequence A1c having 5 consecutive nucleotides each having guanine (G), a nucleotide sequence A2c having 10 consecutive nucleotides each having adenine (A), and the nucleotide sequence A1c, from the 5'-end of the probe and a target-binding substance at the 3'-end thereof. The second probe has a nucleotide sequence A1c having 5 consecutive nucleotides each having cytosine (C) at the 5'-end of the probe and a nucleotide sequence A2 having 10 consecutive nucleotides each having thymine (T) at the 3'-end of the probe. The third probe has the nucleotide sequence A1c at the 5'-end of the probe and the nucleotide sequence A2c at the 3'-end thereof. The nucleotide sequences of the first probe, the second probe, and third probe are listed in sequence listing as SEQ No.1, SEQ No.2, and SEQ No.3 respectively.

In FIG. 2(b), the second probe hybridizes with the first probe. Further, the free second probe binds to the protruded nucleotide sequence A1c of the first probe. The first probe does not have the nucleotide sequences S and Sc in the probe, but the above-mentioned stacking effect can be obtained by hybridizing the first second probe with the first probe. As shown in FIG. 2(c), the second and third probes bind successively to the complex formed in FIG. 2(b), to extend the linear complex for detection. By ligation simultaneous with this extension, the adjacent end of each probe is ligated to form the stable complex for detection as shown in FIG. 2(d).

As shown in FIG. 2(e), the complex for detection is intercalated with an intercalating fluorescent dye such as ethidium bromide, Oregon Green or SYBR GREEN, and by detecting the fluorescence of this dye, the target substance in the sample can be detected. Besides, other known detection methods described above can also be used.

The probe set described above can be provided as a reagent for detecting a target substance in a sample. Alternatively, the probe set can be provided as a reagent kit accommodating the respective probes separately.

EXPERIMENT 1

Figure 3:
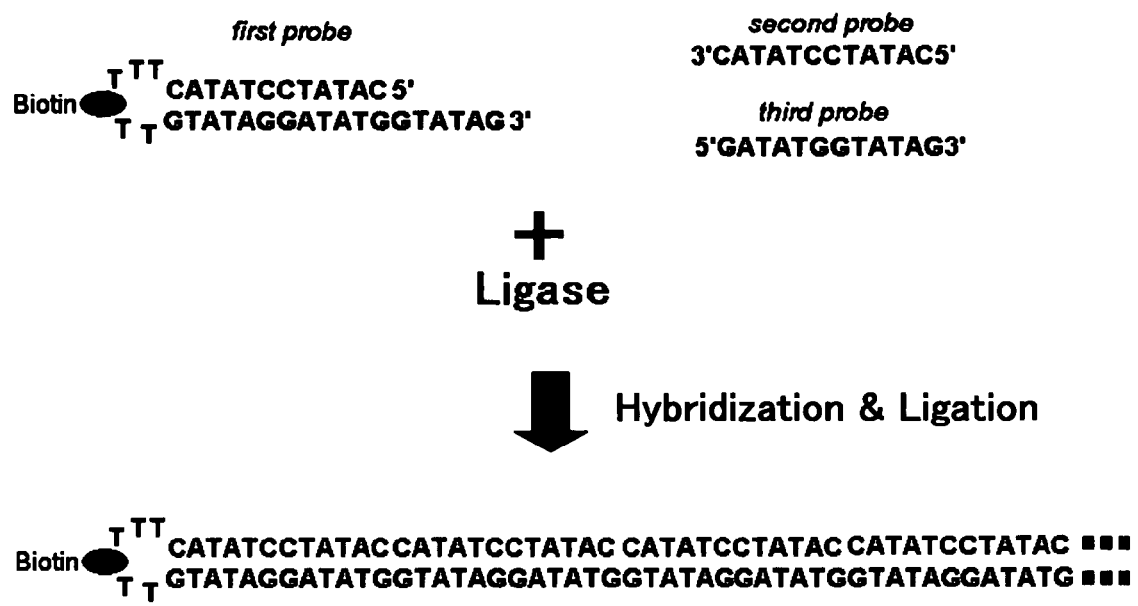
FIG. 3 shows a schematic illustration of the reaction in Experiment 1-1.

<Experiment 1-1>
Whether or not a complex for detection could be formed and extended by hybridization and ligation of a first probe having a stem loop structure, a second probe and a third probe was confirmed by electrophoresis. The reaction in this experiment is schematically shown in FIG. 3.

Materials

1) First probe
(SEQ ID NO.4)
5'-GATATGGTATAGGATATGTT(BIOTIN)TTTCATATCCTATAC-3'

2) Second probe
(SEQ ID NO. 5)
5'-CATATCCTATAC-3'

3) Third probe
(SEQ ID NO. 6)
5'-GATATGGTATAG-3'

4) TE buffer (50 mM Tris-HCl (pH 7.4), 1 mM EDTA)
5) T4 ligase (TAKARA BIO) and attached T4 ligase buffer (×10)
6) Low melting agarose (NuSieve GTG Agarose, TAKARA BIO)
7) 20 bp DNA Ladder (TAKARA BIO)

The 5'-end of each probe was phosphorylated.

Method

The following substances were added to a 0.5-ml sterilized microtube to prepare a 10-μl reaction mixture.
First probe (100 pmol/μl): 1 μl
Second probe (100 pmol/μl): 1 μl
Third probe (100 pmol/μl): 1 μl
T4 ligase: 0.5 μl
T4 ligase buffer (×10): 1 μl
TE buffer: up to 10 μl The formation, extension and ligation reaction of the linear complex for detection were carried out at room temperature for 30 minutes. After the reaction, the reaction mixture was subjected to electrophoresis on 4% agarose gel at 100 V for 15 minutes. After the electrophoresis, the agarose gel was stained with ethidium bromide to confirm whether the complex for detection had been extended or not was confirmed by electrophoresis.

Results

Figure 4:
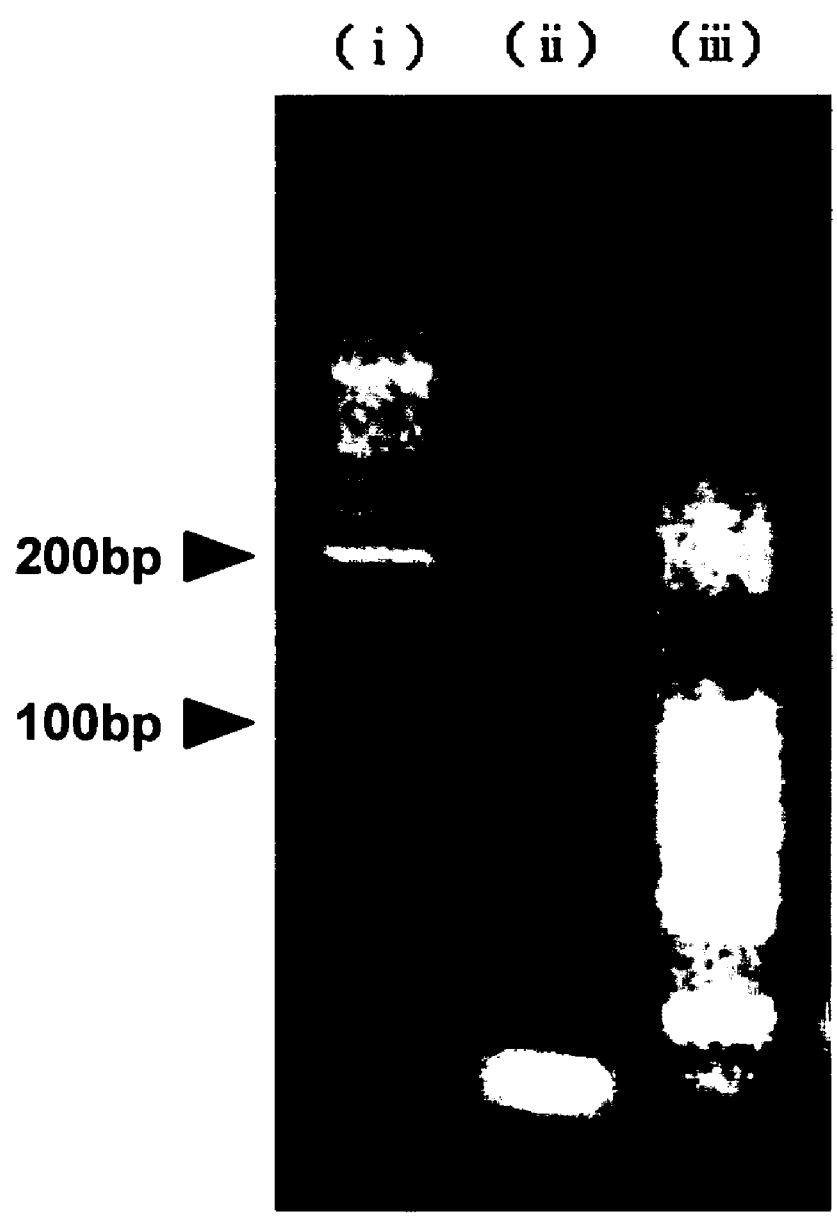
FIG. 4 shows the results of the electrophoresis of Experiment 1-1.

The results of the electrophoresis are shown in FIG. 4. The lane (i) is the result of electrophoresis of 20 bp DNA ladder. The lane (ii) is the result of electrophoresis of only the first probe as a negative control. The lane (iii) is the result of electrophoresis of the reaction mixture in the above experiment. Bands showing a larger molecular weight than that of the band of the first probe observed in the lane (ii) were observed in the lane (iii). The bands in lane (iii) show the extended complex for detection. This indicates that the complex for detection was extended by hybridization and ligation in the above experiment.

<Experiment 1-2>
Whether streptavidin as a target substance fixed on a plate could be detected by forming and extending a complex for detection by hybridization and ligation of a first probe having a stem loop structure, a second probe, and a third probe was confirmed by fluorescence measurement.

Materials
1) SA plate (Black Combiplate 8 Streptavidin Coated; Labsystems)
2) Fluorescent dye YOYO-1 (Molecular Probes)
3) Microplate reader GENios (TECAN)

The same first probe, second probe, third probe, TE buffer, T4 ligase and T4 ligase buffer as in Experiment 1-1 were used.

Method

One μl of the first probe in concentration of 0.02, 0.1, 0.2 and 1 pmol/μl and the following substances were added respectively to four 0.5-ml sterilized microtubes to prepare 50-μl reaction mixture.
Second probe (100 pmol/μl): 5 μl
Third probe (100 pmol/μl): 5 μl
T4 ligase: 2.5 μl
T4 ligase buffer: 5 μl
TE buffer: up to 50 μl The formation, extension and ligation reaction of the linear complex for detection were carried out at room temperature for 15 minutes. After the reaction, each reaction mixture was transferred to each well of an SA plate and left at room temperature for 30 minutes in order to react the formed complex for detection with streptavidin.

Each well of the SA plate was washed 3 times with TE buffer, and then 50 µl of YOYO-1 diluted 10000-fold with TE buffer was added to each well and left at room temperature for 10 minutes to label the complex for detection. Thereafter, the fluorescence emitted by the complex for detection was measured by a microplate reader. The measurement results are shown in a graph of FIG. 5(A).

After the fluorescence measurement, 5 µl each of the second and third probes, 2.5 µl T4 ligase and 5 µl T4 ligase buffer were added to each well of the SA plate, and TE buffer was further added to each well to adjust the total volume to 50 µl. The plate having the reaction mixture was left at room temperature for 30 minutes and then subjected again to extension reaction of the linear complex for detection. The reaction mixture in each well of the plate was stained with YOYO-1 and measured for its fluorescence. The measurement results are shown in graph (B) in FIG. 5.

Separately, a reaction mixture having the same composition as in the reaction mixture prepared in Experiment 1-1 was prepared as a negative control and subjected to staining and fluorescence measurement without conducting the ligation reaction. The measurement results are shown in (N) in FIG. 5.

Results

Figure 5:
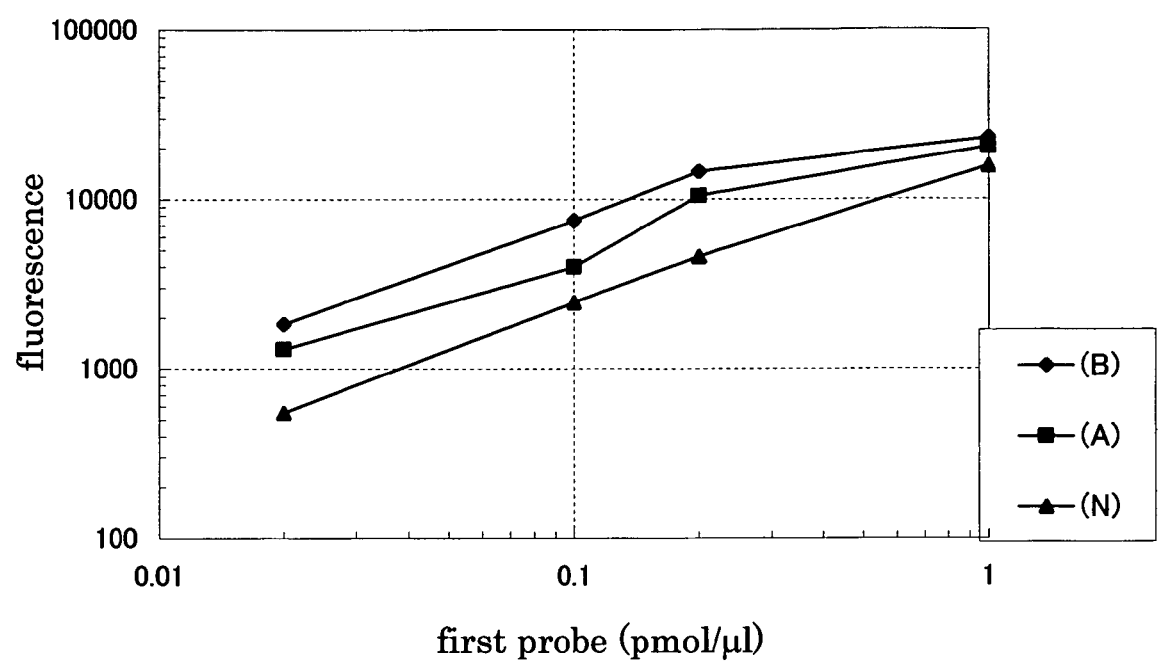
FIG. 5 shows a graph of the measurement results of Experiment 1-2.

As can be seen from FIG. 5, the fluorescence could be detected with a stronger signal by conducting the ligation reaction than without conducting the ligation reaction. The signal could be increased by repeatedly conducting the ligation reaction.

<Experiment 1-3>

Whether thrombin as a target substance fixed on an ELIZA plate could be detected by forming and extending a complex for detection by hybridization and ligation of a first probe having a stem loop structure and containing a sequence having a primary structure of a thrombin aptamer, a second probe for extension, and a third probe, was confirmed by fluorescence measurement.

Materials
1) Thrombin (Enzyme-Research)
2) ELIZA plate (ELIZA plate, Becton Dickinson)
3) First probe containing a sequence having a primary structure of a thrombin aptamer

```
                                                       (SEQ ID NO.7)
5'-GATATGAGTGACTACTGGTTGGTGTGGTTGGGTAGTCACT-3'
```

4) Second probe

```
                                                       (SEQ ID NO.8)
5'-CATATCCATTAG-3'
```

5) Third probe

```
                                                       (SEQ ID NO.9)
5'-GATATGCTAATG-3'
```

6) TBE (45.5 mM Tris-Borate (pH 8.0), 1 mM EDTA (pH 8.0))

The same TE buffer, T4 ligase, T4 ligase buffer, YOYO-1 and microplate reader as in Experiment 1-2 were used. The 5'-end of each probe was phosphorylated.

Method

Each of solutions having thrombin in amounts of 192 pmol, 96 pmol and 48 pmol in 50 µl TBE was added to each well of an ELIZA plate and then incubated at 37° C. for 2 hours to immobilize thrombin on the plate. Thereafter, each well of the plate was washed 3 times with TBE buffer to prepare a thrombin plate. Fifty µl TE buffer containing 5 µl of 100 pmol/µl first probe was added to each well of the thrombin plate and left at room temperature for 1 hour to bind thrombin to the first probe. Each well of the plate was washed 3 times with TE buffer, and then 50 µl YOYO-1 diluted 10000-fold with TE buffer was added to each well and subjected to fluorescence staining by leaving it for 10 minutes. Thereafter, the fluorescence emitted by the thrombin/first probe complex was measured by the microplate reader. The measurement results are shown in graph (A) of FIG. 6.

Then, each well was washed 3 times with TE buffer, and the following substances were added to each well to prepare 50 µl reaction mixture.

Second probe (100 pmol/µl): 5 µl
Third probe (100 pmol/µl): 5 µl
T4 ligase: 2.5 µl
T4 ligase buffer: 5 µl
TE buffer: up to 50 µl The plate having this reaction mixture was left at room temperature for 15 minutes, whereby the formation, extension and ligation reaction of the linear complex for detection were carried out. After the reaction, each well was washed 3 times with TE buffer, and then 50 µl of YOYO-1 diluted 10000-fold with TE buffer was added thereto and subjected to fluorescence staining by leaving it for 10 minutes. Thereafter, the fluorescence emitted by the complex for detection was measured by the microplate reader. The measurement results are shown in graph (B) in FIG. 6. A schematic illustration of the complex for detection formed in this experiment is shown in FIG. 7.

Results

Figure 6:
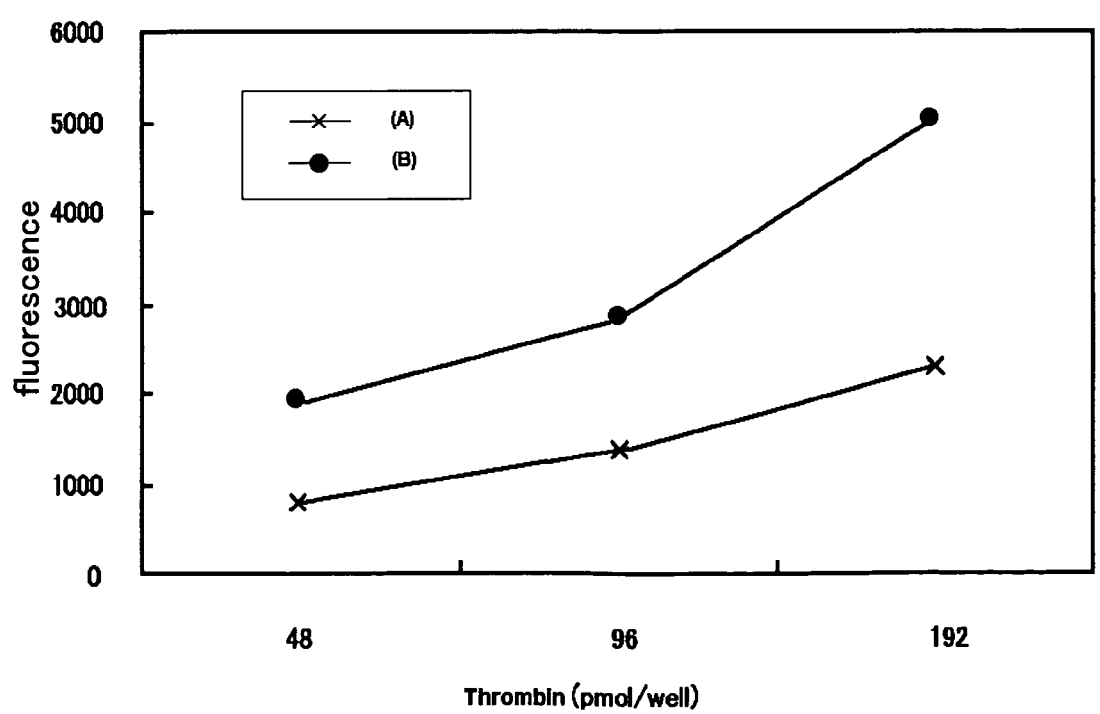
FIG. 6 shows a graph of the measurement results of Experiment 1-3.
Figure 7:
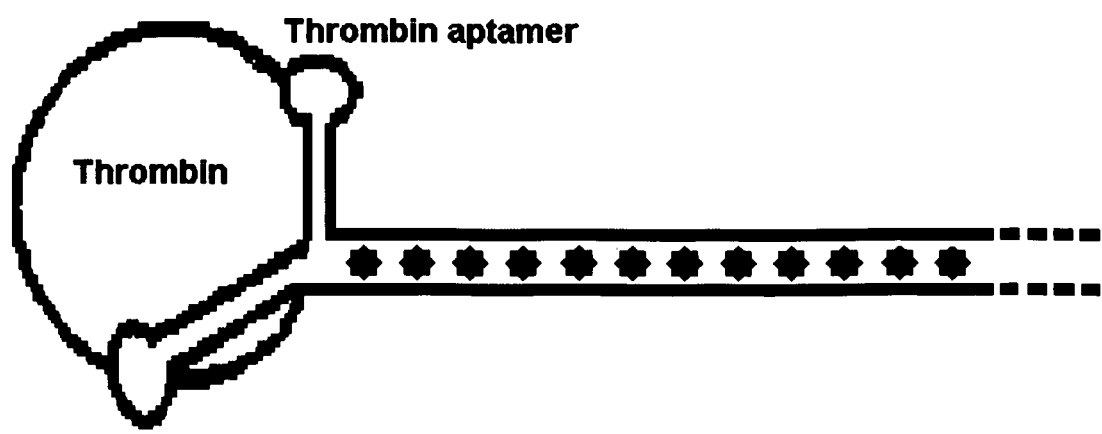
FIG. 7 shows a schematic illustration of the complex for detection formed in Experiment 1-3.

As can be seen from FIG. 6, stronger fluorescence could be detected in (B) than (A). It was confirmed that the signal could be amplified by formation and extension of the complex for detection, to detect the target substance more highly sensitively.

EXAMPLE 2

Probe Set Forming a Cyclic Complex for Detection

Probes having the following features can be used to form a cyclic complex for detection in order to detect a target substance in a sample.

(1) First Probe

The first probe has a target-binding substance and base sequences A1c and A2c. The base sequences A1c and A2c are adjacent to each other. Preferably, the first probe has a base sequence S and a base sequence Sc hybridizable with the base sequence S.

(2) Second Probe

The second probe has base sequences A1, A2, B1 and B2. The base sequences A1 and A2 are located at both ends of the second probe respectively. The base sequences B1 and B2 are adjacent to each other. An intervening part is present between the base sequences A1 and B1. An intervening part is also present between the base sequences B2 and A2. When the intervening part is a base sequence, the base sequence of this intervening part is designed not to hybridize with any of the base sequences A1, A1c, A2, A2c, B1, B1c, B2, B2c, S and Sc.

(3) Third Probe

The third probe has base sequences B1c, B2c, A1c and A2c. The base sequences B1c and B2c are located at both ends of the third probe respectively. The base sequences A1c and A2c are adjacent to each other. An intervening part is present between the base sequences B1c and A1c. An intervening part is also present between the base sequences A2c and B2c.

Among the base sequences described above, a pair of base sequences A1 and A1c, a pair of base sequences A2 and A2c, a pair of base sequences B1 and B1c and a pair of base sequences B2 and B2c are designed respectively to be hybridizable with each other. Thus, the second and third probes hybridize cyclicly with the first probe bound to the target substance, to form a complex for detection. The type of base constituting each base sequence is not particularly limited.

Both ends of the second probe and both ends of the third probe, constituting the complex for detection, are preferably ligated. Durability against decomposition and washing can thereby be increased. When the base sequence of the probe is a base sequence of DNA or RNA, the ends of the probe can be ligated by a ligase. When the base sequence of the probe is an artificial nucleic acid, the probe can be ligated by a known method such as photoligation described above.

The first probe preferably has a plurality of the sequences A1c and A2c adjacent to each other. The second probe preferably has a plurality of the base sequences B1 and B2 adjacent to each other. The third probe preferably has a plurality of the base sequences A1c and A2c adjacent to each other. In this case, plural second probes can bind to the first probe, and plural third probes can bind to these second probes. Further, free second probes can bind to these third probes. The number of probes binding to the complex for detection can thereby be exponentially increased to detect the target substance with a stronger signal.

Although the length of the intervening part possessed by each probe is not particularly limited, the length is preferably 3 bases or more. When the intervening part in each of these probes is long, a ring of the probes upon forming the complex for detection is large, and a plurality of probes bind structurally easily to one probe. Accordingly, the intervening part is preferably longer.

Figure 8:
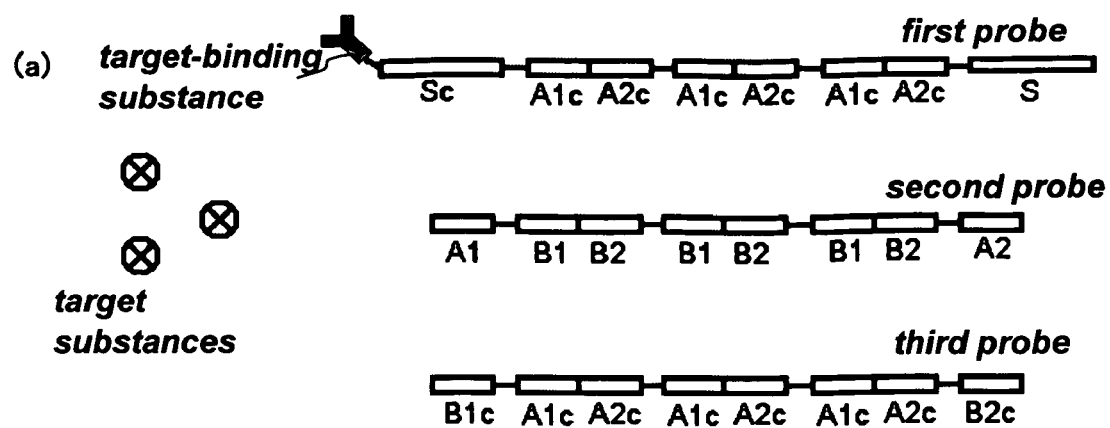
FIG. 8(a) shows a schematic illustration of target substances and the first, second and third probes.
FIG. 8(b) shows a schematic illustration of the minimum unit of the complex for detection.
FIG. 8(c) shows a schematic illustration of the complex for detection to which a fluorescent probe is bound.
Figure 8:
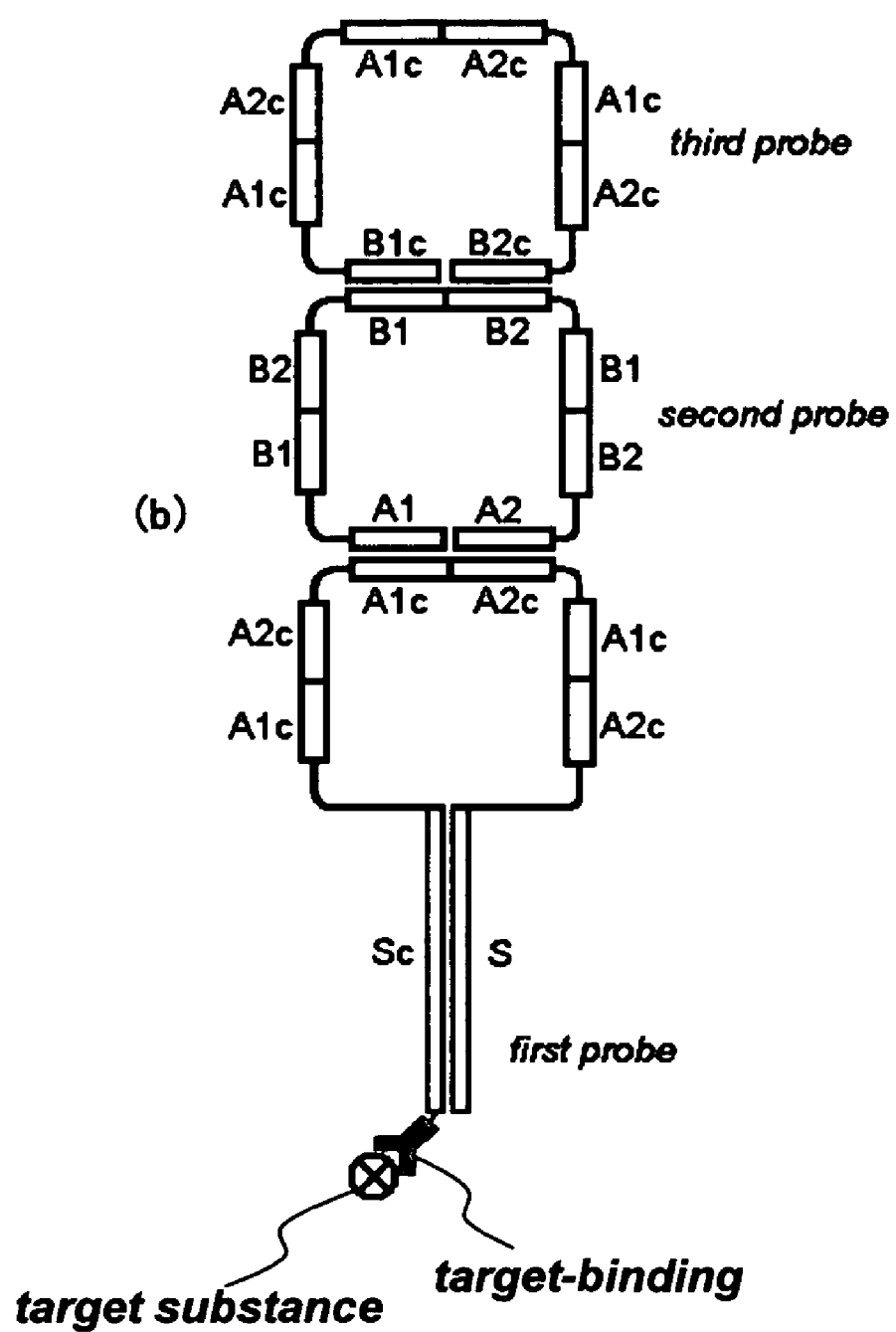

Hereinafter, the method of detecting a target substance by the probe set forming a cyclic complex for detection is described in detail by reference to FIG. 8.

FIG. 8(a) is a schematic illustration of target substances and the first, second and third probes. FIG. 8(b) is a schematic illustration of the minimum unit of the complex for detection. FIG. 8(c) is a schematic illustration of the complex for detection to which a fluorescent probe is bound.

As shown in FIG. 8(a), the first probe has the base sequences S and Sc at both ends thereof respectively, and has a target-binding substance at the end of the base sequence Sc. The first probe has 3 base sequences of the adjacent base sequences A1c and A2c in the probe. The second probe has the base sequences A1 and A2 at both ends thereof respectively, and has 3 base sequences of the adjacent base sequences B1 and B2 in the probe. The third probe has the base sequences B1c and B2c at both ends thereof respectively, and has 3 base sequences of the adjacent base sequences A1c and A2c in the probe.

When the target substance and the first, second and third probes are mixed, the first probe binds to the target substance. The base sequences A1 and A2 of the second probe hybridize respectively with the base sequences A1c and A2c of the first probe. Then, the base sequences B1c and B2c of the third probe hybridize respectively with the base sequences B1 and B2 of the second probe bound to the first probe. The complex for detection as shown in FIG. 8(b) is thereby formed.

A known method using an intercalating fluorescent dye, a radioisotope, a fluorescent/luminescent/coloring substance, etc. such as in the method of detection using the linear complex for detection in Example 1 can be used as the detection method.

When the intervening part of each probe is a nucleic acid, the signal can be obtained by using labeled nucleic acid probe (hereinafter, referred to as "LNA probe"). LNA probe is prepared by bonding a label (such as a radioisotope, a fluorescent/luminescent/coloring substance or the like) to a single-stranded nucleic acid probe having a base sequence capable of binding to the intervening part. As the intervening part remains single-stranded even if the cyclic complex for detection is formed, as shown in FIG. 8(c), the LNA probe can hybridize the intervening part of each probe constituting the complex for detection. Emitted radiation, fluorescence/luminescence/coloration etc from LNA probes which bind to the complex for detection can be used as the signal.

When the intervening part of each probe is nucleic acid, and intercalating fluorescent dye is used, the signal can be increased by using single-stranded nucleic acid probe (hereinafter, referred to as "NA probe") having a base sequence capable of binding to the intervening part. As the intervening part remains single-stranded even if the cyclic complex for detection is formed, the NA probe can hybridize the intervening part of each probe constituting the complex for detection. By hybridizing the intervening part with NA probes, the intervenign part and the NA probe become double-stranded. Therefore, the double-stranded region of the complex for detection that intercalating dye can bind to increases more than that of the complex for detection without using the NA probe, and the stronger signal can be obtained.

EXPERIMENT 2

<Experiment 2-1>

Whether or not the first and second probes were bound to each other by hybridization and ligation of the first probe having a stem loop structure and biotin in the sequence thereof and the second probe was confirmed by electrophoresis. The reaction in this experiment is schematically shown in FIG. 9.

Materials

1) First probe (SEQ ID NO. 10)
5'-BIOTIN-GGGCCGGGCCGGGCCTTTTTTTTTTGTGAGTAGATAGTTT

TTTTTTTGGCCCGGCCCGGCCC-3'

2) Second probe (SEQ ID NO. 11)
5'ACTCACTTTTTGTACATACTCTTTTTGTACATACTCTTTTTGTACATA

CTCTTTCTATCT-3'

The same TE buffer, T4 ligase, T4 ligase buffer, low melting agarose and 20 bp DNA ladder as in Experiment 1-1 were used. The 5'-end of each probe was phosphorylated.

Method

The following substances were added to 0.5-ml sterilized microtubes (i) to (iii).

Microtube (i)
  20 bp DNA ladder

Microtube (ii)
  First probe (100 pmol/μl): 0.5 μl
  Second probe (100 pmol/μl): 0.5 μl
  T4 ligase: 0.5 μl
  T4 ligase buffer (×10): 1 μl
  TE buffer: up to 10 μl Microtube (iii)
  First probe (100 pmol/μl): 0.5 μl
  TE buffer: up to 10 μl Microtubes (ii) and (iii) were left at room temperature for 30 minutes. Microtubes (i) to (iii) were subjected to electrophoresis on 4% agarose gel at 100 V for 15 minutes. After the electrophoresis, the agarose gel was stained with ethidium bromide to confirm whether the second probe was bound to the first probe.

Results

Figure 10:
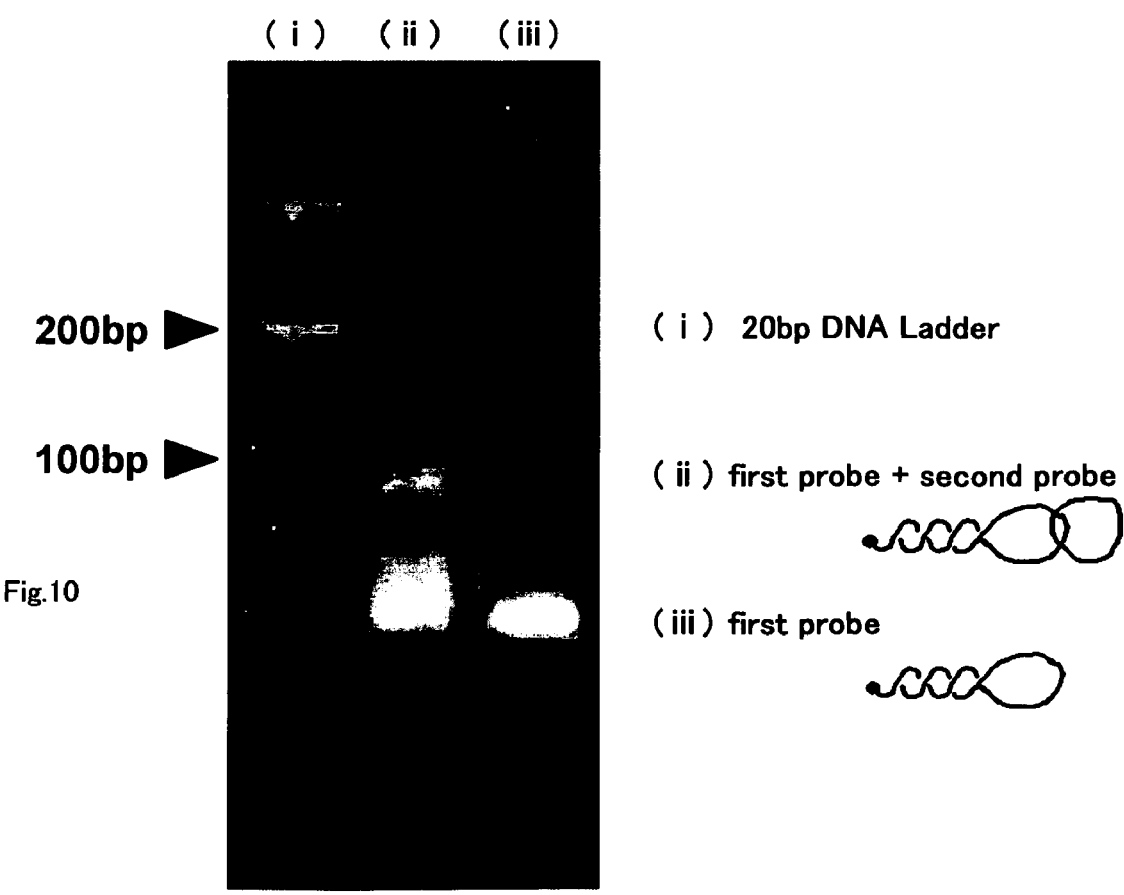
FIG. 10 shows the results of the electrophoresis of Experiment 2-1.

The results are shown in FIG. 10. FIG. 10 is a photograph showing the result of electrophoresis in the above experiment. The DNA ladder in microtube (i) was electrophoresed on lane (i), the reaction mixture in the microtube (ii) on lane (ii), and the mixture in the microtube (iii) on lane (iii). In lane (ii), a band showing a substance having a higher molecular weight than that of the first probe was observed in addition to a band showing the first probe only. This band shows a substance wherein the first and second probes were bound to each other. Accordingly, it was confirmed by the above experiment that the second probe hybridized with the first probe.

<Experiment 2-2>

Whether or not the signal was amplified by binding the probes cyclicly to the complex for detection was confirmed by fluorescence measurement.

Materials

1) Fluorescent probe
                                               (SEQ ID NO: 12)
5'-FITC-CTATCTCACTCACAAACTATCTACTCAC-3'

2) Third probe
                                               (SEQ ID NO. 13)
5'- GTACAATTTGTGAGTAGATAGTTTGTGAGTAGATAGTTTGTGAGTA

GATAGTTTGAGTAT-3'

The same first probe, second probe, T4 ligase, T4 ligase buffer and TE buffer as in Experiment 2-1 were used. The same SA plate and microplate reader as in Experiment 1-2 were used. The 5'-end of the third probe has been phosphorylated.

Method

Forty-nine μl TE buffer was introduced into each of four 0.5-ml sterilized microtubes, and 1 μl of the first probe in concentration of 0.1, 0.2, 1 and 2 pmol/μl respectively was added thereto to form a reaction mixture. Each reaction mixture was transferred to each well of an SA plate and left at room temperature for 30 minutes to react streptavidin in the SA plate with the first probe.

After the reaction, each well of the SA plate was washed 3 times with TE buffer. After washing, the following substances were added to each well and subjected to hybridization and ligation at room temperature for 30 minutes.
  Second probe (100 pmol/μl): 10 μl
  T4 ligase: 5 μl
  T4 ligase buffer: 10 μl
  TE buffer: up to 100 μl Then, each well of the SA plate was washed 3 times with TE buffer. After washing, the following substances were added to each well and subjected again to hybridization and ligation at room temperature for 30 minutes.
  Third probe (100 pmol/μl): 10 μl
  T4 ligase: 5 μl
  T4 ligase buffer: 10 μl
  TE buffer: up to 100 μl Then, each well of the SA plate was washed 3 times with TE buffer. After washing, a staining solution prepared by mixing 1 μl of 100 pmol/μl fluorescent probe with 99 μl TE buffer was added thereto and left at room temperature for 15 minutes to carry out fluorescence staining. Each well of the SA plate was washed 3 times with TE buffer and measured for its fluorescence by the microplate reader. The measurement results are shown in graph (A) in FIG. 11.

On the other hand, a reaction mixture not subjected to hybridization and ligation was prepared as a negative control. Forty-nine μl TE buffer was introduced into each of four 0.5-ml sterilized microtubes, and 1 μl of the first probe in concentration of 0.1, 0.2, 1 and 2 pmol/μl was added thereto to prepare each reaction mixture. Each reaction mixture was transferred to each well of an SA plate and left at room temperature for 30 minutes to react streptavidin in the SA plate with the first probe. Then, each well of the SA plate was washed 3 times with TE buffer. After washing, a staining solution prepared by mixing 1 μl of 100 pmol/μl fluorescent probe with 99 μl TE buffer was added thereto and subjected to fluorescence staining at room temperature for 15 minutes. Each well of the SA plate was washed 3 times with TE buffer and measured for its fluorescence by the microplate reader. The measurement results are shown in graph (N) in FIG. 11.

Results

Figure 11:
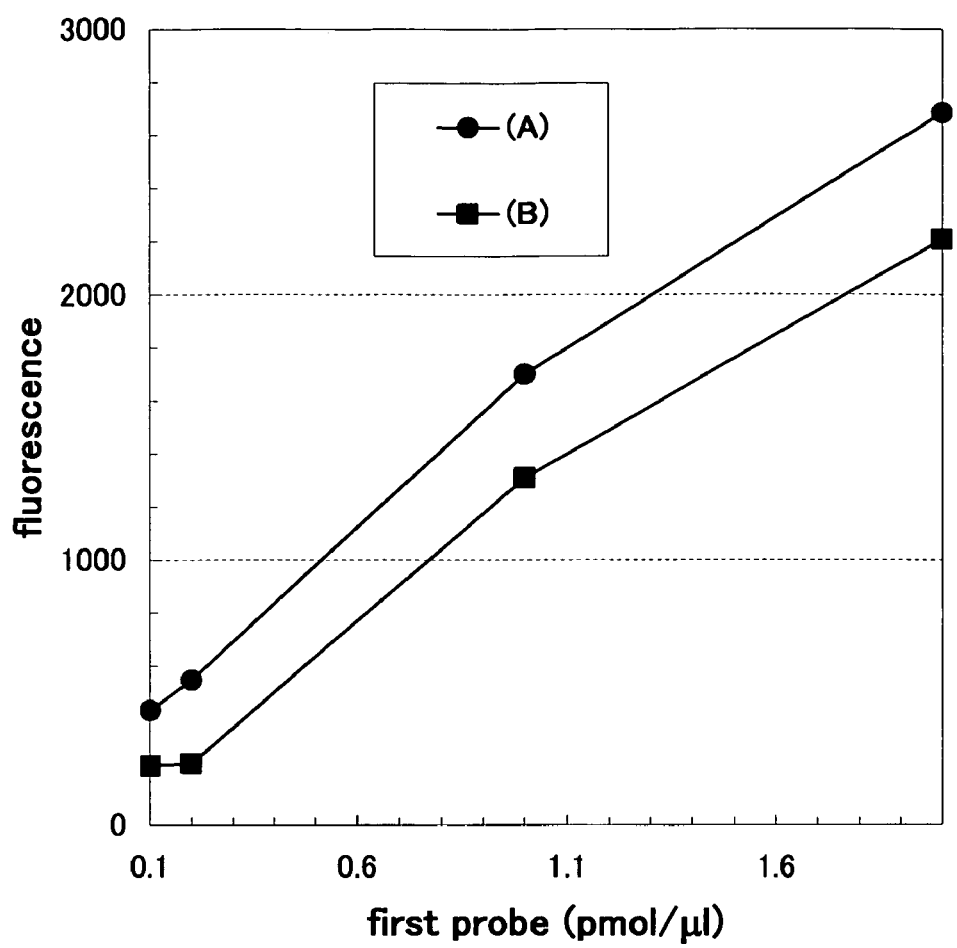
FIG. 11 shows a graph of the measurement results of Experiment 2-2.

As can be seen from FIG. 11, stronger fluorescence could be detected by measurement with the complex for detection formed by hybridization and ligation than by measurement without conducting hybridization and ligation. Accordingly, it was found that the target substance could be detected with a stronger signal than by hybridization and ligation of the probe set in this embodiment.

What is claimed is:

1. A probe set comprising:
a first probe having:
a target-binding substance which can bind a target substance,
a base sequence X1,
a base sequence Zc, and
a base sequence Z hybridizable with the base sequence Zc,
a second probe having a base sequence X1c and a base sequence X2c, the base sequence X1c being hybridizable with the base sequence X1, and
a third probe having a base sequence X2 hybridizable with the base sequence X2c.

2. The probe set of claim 1, wherein the third probe has the base sequence X1 hybridizable with the base sequence X1c.

3. The probe set of claim 1, wherein the base sequence Zc is adjacent to the base sequence X1.

4. A probe set comprising:
a first probe having:
a target-binding substance which can bind a target substance, and
a base sequence X1,
a second probe having a base sequence X1c and a base sequence X2c, the base sequence X1c being hybridizable with base sequence X1, and
a third probe having a base sequence X2 hybridizable with the base sequence X2c,
wherein
the base sequence X1 of the first probe is located at the end of the first probe,
the base sequence X1c of the second probe is located at one end of the second probe,
the base sequence X2c of the second probe is located at the other end of the second probe, and
the base sequence X2 of the third probe is located at the end of the third probe.

5. The probe set of claim 1, wherein the target substance is a nucleic acid or protein, and the target-binding substance is a nucleic acid or antibody.

6. A reagent for detection of a target substance, which comprises the probe set of claim 1.

7. A reagent kit comprising a reagent containing the probe set of claim 1 and a reagent containing a ligase.

8. A method for detecting a target substance, comprising steps of:
(a) preparing the probe set of claim 1,
(b) binding the target-binding substance to a target substance,
(c) hybridizing the second probe with the first probe, and hybridizing the third probe with the second probe to form a complex comprising the target substance, the first probe, the second probe and the third probe, and
(d) detecting the target substance by detecting the complex.

9. The method of claim 8, which is carried out in the order of the steps (a), (b), (c) and (d).

10. The method of claim 8, which is carried out in the order of the steps (a), (c), (b) and (d).

11. The method of claim 8, which comprises a step of ligating the end of the probe with the end of its adjacent probe.

12. A probe set comprising:
a first probe having:
a target-binding substance which can bind a target substance,
a base sequence X12 of base sequences X1 and X2 adjacent to each other,
a base sequence Z, and
a base sequence Zc hybridizable with the base sequence Z,
a second probe having:
a base sequence X1c hybridizable with the base sequence X1 at one end,
a base sequence X2c hybridizable with the base sequence X2 at the other end, and
a base sequence Y12c of base sequences Y1c and Y2c adjacent to each other, and
a third probe having:
a base sequence Y1 hybridizable with the base sequence Y1c at one end, and
a base sequence Y2 hybridizable with the base sequence Y2c at the other end.

13. The probe set of claim 12, wherein the third probe has the base sequence X12.

14. The probe set of claim 12, wherein the first probe has a plurality of the base sequences X12, the second probe has a plurality of the base sequences Y12c, and the third probe has a plurality of the base sequences X12.

15. A reagent for detection of a target substance, comprising the probe set of claim 12.

16. A reagent kit comprising a reagent containing the probe set of claim 12 and a reagent containing a ligase.

17. A method for detecting a target substance, comprising steps of:
(a) preparing the probe set of claim 12,
(b) binding the target-binding substance to the target substance,
(c) hybridizing the second probe with the first probe, and hybridizing the third probe with the second probe to form a complex comprising the target substance, the first probe, the second probe and the third probe, and
(d) detecting the target substance by detecting the complex.

18. The method of claim 17, which is carried out in the order of the steps (a), (b), (c) and (d).

19. The method of claim 17, which is carried out in the order of the steps (a), (c), (b) and (d).

20. The method of claim 17, which comprises:
a step of ligating both ends of the second probe and ligating both ends of the third probe after the step (c).

21. The probe set of claim 1, wherein
the first probe comprises two single-strand base sequences, wherein one is the base sequence Z and the other is the base sequence Zc,
the base sequence Z comprises the base sequences X1 and X2,
the base sequence Zc is the same as the second probe, and
the target-binding substance is bound to either the base sequence Z or Zc.

22. The probe set of claim 1, wherein
the target-binding substance is located at the end of base sequence Z or Zc,
the base sequence X1 of the first probe is adjacent to the base sequence Z or Zc,
the base sequence X1 of the first probe is located at the end of the first probe,
the base sequence X1c of the second probe is located at one end of the second probe,
the base sequence X2c of the second probe is located at the other end of the second probe,
the base sequence X2 of the third probe is located at the end of the third probe.

* * * * *